United States Patent
Chang et al.

(10) Patent No.: US 6,368,882 B1
(45) Date of Patent: Apr. 9, 2002

(54) METHOD FOR DETECTING ORGANIC CONTAMINATION BY USING HEMISPHERICAL-GRAIN POLYSILICON LAYER

(75) Inventors: Leon Chang; Chien-Hung Chen, both of Taipei (TW)

(73) Assignee: Mosel Vitelic Inc., Hsinchu (TW)

( * ) Notice: Subject to any disclaimer, the term of this patent is extended or adjusted under 35 U.S.C. 154(b) by 0 days.

(21) Appl. No.: 09/531,233

(22) Filed: Mar. 21, 2000

(30) Foreign Application Priority Data

Nov. 1, 1999 (TW) .......................... 088118993

(51) Int. Cl.$^7$ .......................... H01L 21/00; H01L 21/66
(52) U.S. Cl. ............................ 438/7; 438/14
(58) Field of Search ................. 438/7, 12, 14

(56) References Cited

U.S. PATENT DOCUMENTS

| | | | | |
|---|---|---|---|---|
| 4,964,919 A | * | 10/1990 | Payne ........................... | 134/2 |
| 5,928,969 A | * | 7/1999 | Li et al. ...................... | 438/753 |
| 5,970,312 A | * | 10/1999 | Nam et al. ..................... | 438/14 |
| 6,046,061 A | * | 4/2000 | Tsao et al. .................... | 438/16 |
| 6,117,692 A | * | 9/2000 | Kim et al. ..................... | 438/14 |
| 6,171,872 B1 | * | 1/2001 | Lowrey et al. ................ | 438/10 |
| 6,177,127 B1 | * | 1/2001 | Weimer et al. ................ | 427/8 |
| 6,194,234 B1 | * | 2/2001 | Huang et al. ................. | 438/14 |

OTHER PUBLICATIONS

Vandervorst et al., "Advanced characterisation: an indispensable tool for understanding ultra clean processing", Microelectronic Engineering, vol. 28, 1995, pp. 27–34.*

Sakai et al., "Crystallization of Amorphous Silicon with Clean Surfaces", Japanese Journal of Applied Physics Letters, vol. 30, No. 6A, Jun. 1991, pp. L941–L943.*

Watanabe et al., "An Advanced Technique for Fabricating Hemispherical–Grained (HSG) Silicon Storage Electrodes", IEEE Transactions on Electron Devices, vol. 42, No. 2, Feb. 1995, pp. 295–300.*

Kitajima et al., "Requirements for Contamination Control in the Gigabit Era", IEEE Transactions on Semiconductor Manufacturing, vol., 10, No. 2, 1997, pp. 267–272.*

* cited by examiner

*Primary Examiner*—Long Pham
*Assistant Examiner*—William David Coleman
(74) *Attorney, Agent, or Firm*—Kinney & Lange, P.A.

(57) ABSTRACT

The present invention discloses a method to detect organic contamination in process environment of integrated circuits by using hemispherical-grain polysilicon layer that is formed in the process environment. The organic residue will contaminates the substrate which the hemispherical-grain polysilicon layer is formed thereon so as that the grain size of the polysilicon layer is between about 0.2 to 0.4 micrometers. The grain size of the hemispherical-grain polysilicon layer that is fabricated in a clean process environment is between about 0.5 to 0.8 micrometers. In other words, if organic contamination is residual in process environment, the grain size of the hemispherical-grain polysilicon layer that is fabricated in the process environment is smaller than a certain size to determine that the process environment is contaminated by organic contamination.

14 Claims, 2 Drawing Sheets

METHOD FOR DETECTING ORGANIC CONTAMINATION BY USING HEMISPHERICAL-GRAIN POLYSILICON LAYER

FIELD OF THE INVENTION

The present invention relates to a method for detecting organic contamination in a process equipment of manufacturing integrated circuits, more specifically, to a method for detecting organic contamination in a process equipment of manufacturing integrated circuits by using the fabrication of hemispherical polysilicon grains in the integrated circuits.

Background of the Invention

During the fabrication of integrated circuits, several kinds of contamination contaminates silicon wafers or the integrated circuits on the silicon wafers. The kinds of contamination include conductive-dopant contamination, metal impurity, native oxide contamination and organic impurity contamination. In general, these kinds of contamination seriously influents the yield for manufacturing integrated circuits on wafers. Thus, how to detect the contamination on silicon wafers or to clean the contamination on wafers becomes a very important issue. In the following descriptions, the method to detect these kinds of contamination will be explained.

At first, conductive-dopant contamination often occurs, as the ion implantation process is performed to dope silicon wafers, which integrated circuits are formed thereon, during the fabrication of the integrated circuits. The conductive dopant will be a contamination source of silicon wafers. Generally, a method to detect the conductive-dopant impurity is performed by using X-ray detecting technique or measuring resistive constant to determine whether the silicon wafers are suffered from the conductive-dopant contamination. Furthermore, metal-impurity contamination can be detected by specified detecting technique and it still can be effectively found.

About the contamination source of native oxide, conventional techniques can be effectively detected. The method for removing the native-oxide contamination is to clean the surface of silicon wafers by using HF solution that can easily remove the native oxide layer on the silicon wafers.

Special equipment is needed for detecting organic contamination on silicon wafers. Nevertheless, the special equipment can not be located in a clean room. If silicon wafers would be detected whether organic impurity contaminates the surface of the silicon wafers, the wafers must be moved out of the cleaning room, which the integrated circuits on the silicon wafers are fabricated therein, for the measurement of organic contamination. Moreover, the special equipment can not rapidly detect the organic contamination on silicon wafers for the large throughput of integrated circuits. Additionally, as silicon wafers are moved out of cleaning rooms, the silicon wafers will suffered from organic contamination. It is hard to determine whether organic contamination is formed on the surface of silicon wafers, in other words, organic contamination on silicon wafers can not be precisely measured.

During the fabrication of integrated circuits in cleaning rooms, silicon wafers, which the integrated circuits are formed thereon, are put into wafer cassettes for the transferring in batch. Before silicon wafers are loaded into wafer cassettes, the cassettes are cleaned by using acetone solution to remove the contamination on wafer cassettes. Nevertheless, acetone solution is indicated as organic material. Thus, after the cleaning process by using acetone solution, the wafer cassettes are cleaned by using dilute-ion (DI) water for removing the acetone residue on the cassettes. But, the above cleaning process can not completely remove the acetone residue on the cassettes. Consequently, organic contamination on the cassettes is residual after the acetone cleaning process. As silicon wafers are loaded into the wafer cassettes, the silicon wafers are contaminated by the acetone residue on the cassettes and the acetone residue is indicated as a main source of organic contamination.

According to the above discussion, there is no effective and rapid method to detect organic contamination on silicon wafers in the technique of fabricating integrated circuits. The present organic detecting technique is performed out of a cleaning room and can not in-situ detect organic contamination on silicon wafers. Therefore, an in-situ organic contamination detecting method in a cleaning room is needed for in-situ improving the process environment of integrated circuits.

SUMMARY OF THE INVENTION

The present invention provides a method for detecting organic contamination in a process environment by using the deposition of hemispherical polysilicon grains. A semiconductor substrate is provided and an amorphous silicon layer is deposited on the substrate. Subsequently, the amorphous silicon layer is transformed into a hemispherical-grain polysilicon layer on the substrate. The grain size of the hemispherical-grain polysilicon layer is measured to determine whether the organic contamination is residual on the substrate.

The present invention provides a preferred embodiment disclosing that the grain size of the hemispherical-grain polysilicon layer is measured, as the grain size is between about 0.2 to 0.4 micrometers, the organic contamination is residual on the semiconductor substrate; as the grain size is between about 0.5 to 0.8 micrometers, the organic contamination is not residual on the semiconductor substrate.

The present invention provides a preferred embodiment providing a cleaning process performed on the semiconductor substrate to remove the organic contamination on the semiconductor substrate before the hemispherical-grain polysilicon layer is formed.

The present invention provides a preferred embodiment disclosing the cleaning process cleans the semiconductor substrate by using acetone solution.

The present invention provides a preferred embodiment disclosing organic contamination comprises the contamination of acetone solution.

In a preferred embodiment of the present invention, the organic contamination has influence with the growth of the hemispherical-grain polysilicon layer, so that the grain size of the hemispherical-grain polysilicon layer is smaller than 0.4 micrometers.

In a preferred embodiment of the present invention, the semiconductor substrate is suffered from the organic contamination, which is indicated as the process environment is suffered from the organic contamination.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention discloses a method to detect organic contamination in process environment of integrated circuits by using hemispherical-grain polysilicon layer that is formed in the process environment. The organic residue will contaminates the substrate which the hemispherical-grain polysilicon layer is formed thereon so as that the grain size of the polysilicon layer is between about 0.2 to 0.4 micrometers. The grain size of the hemispherical-grain polysilicon layer that is fabricated in a clean process environment is between about 0.5 to 0.8 micrometers. In other words, if organic contamination is residual in process environment, the grain size of the hemispherical-grain polysilicon layer that is fabricated in the process environment is smaller than a certain size to determine that the process environment is contaminated by organic contamination.

Figure 3:
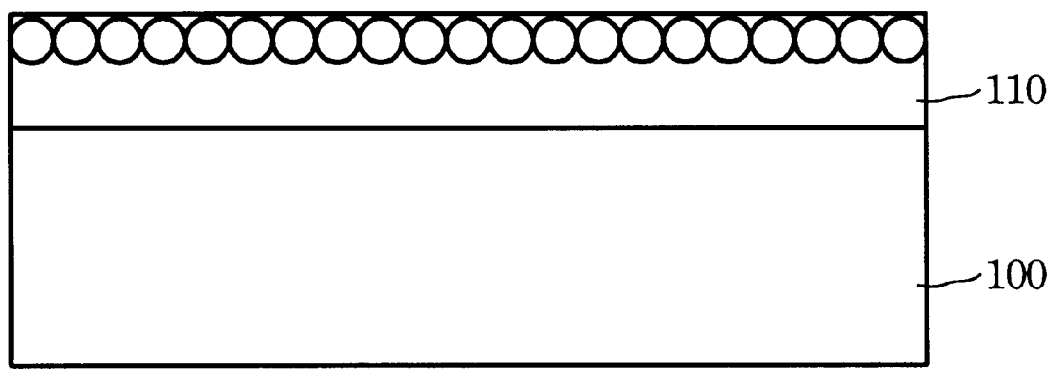
FIG. 3 shows a cross-section view of a semiconductor substrate in accordance with the present invention, wherein a cleaning process is performed to remove the native oxide layer on the surface of the semiconductor substrate.
Figure 4:
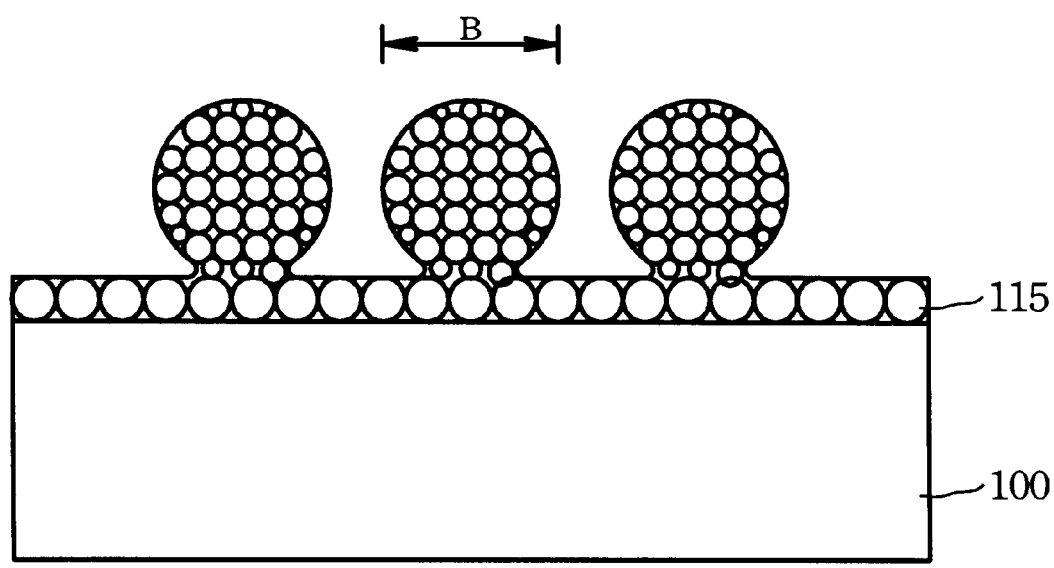
FIG. 4 shows a cross-section view of a semiconductor substrate in accordance with the present invention, wherein hemispherical-grain polysilicon layer is formed on a semiconductor substrate, since no organic contamination residue is formed on the surface of the semiconductor substrate, the hemispherical grain of the polysilicon layer in accordance with the present invention has a larger grain size than that in accordance with the prior art.

Referring to FIG. 3, a semiconductor substrate 100 is provided to serve as a base of fabricating hemispherical-grain polysilicon layer thereon. Subsequently, an amorphous silicon layer 110 is conformally deposited on a top surface of the semiconductor substrate 100 by using a conventional depositing process. Referring to FIG. 4, the amorphous silicon layer 110 is transformed to form a hemispherical-grain polysilicon layer 115 on the semiconductor substrate 100. Afterwards, the grain size B of the hemispherical-grain polysilicon layer 115 is measured to determine whether the semiconductor substrate 100 is suffered from organic contamination.

In a preferred embodiment of the present invention, as the hemispherical-grain polysilicon layer 115 has a grain-size of between about 0.2 to 0.4 micrometers, the semiconductor substrate 100 is contaminated in process environment which integrated circuits on the substrate 100 are fabricated therein. If the grain size of the hemispherical-grain polysilicon layer 115 is between about 0.5 to 0.8 micrometers, the semiconductor 100 is not contaminated by any organic contamination.

In the method of fabricating hemispherical-grain polysilicon layer of the present invention, before the deposition of the layer, a cleaning process is performed for removing the organic contamination on the semiconductor substrate. Furthermore, the cleaning process uses acetone solution to clean the surface of the semiconductor substrate. The organic contamination source in process environment mainly results from the acetone solution adapted in the above described cleaning process and the organic contamination influents the growth of the hemispherical polysilicon grain which has not a grain size being larger than 0.4 micrometers. According to the above discussion, the semiconductor substrate suffered from organic contamination means that the process environment of the semiconductor substrate is suffered from organic contamination.

Figure 1:
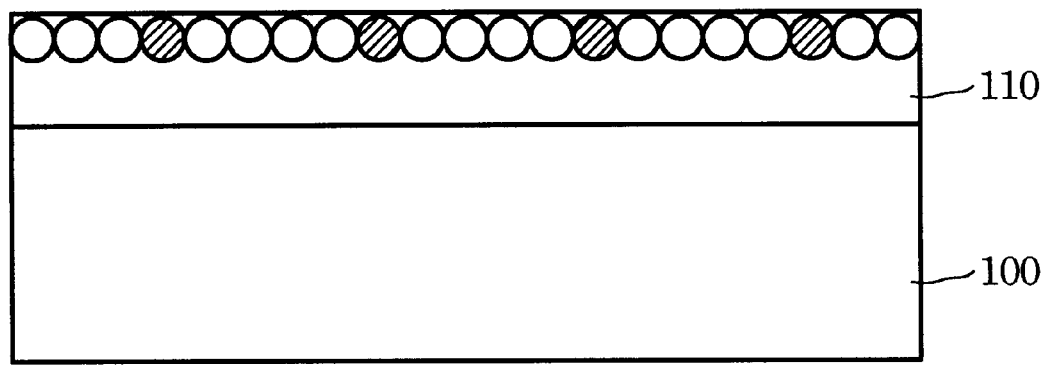
FIG. 1 shows a cross-section view of a semiconductor substrate in accordance with the prior art, wherein organic contamination residues are formed on the surface of the semiconductor substrate to contaminate the partial silicon atoms on the substrate.
Figure 2:
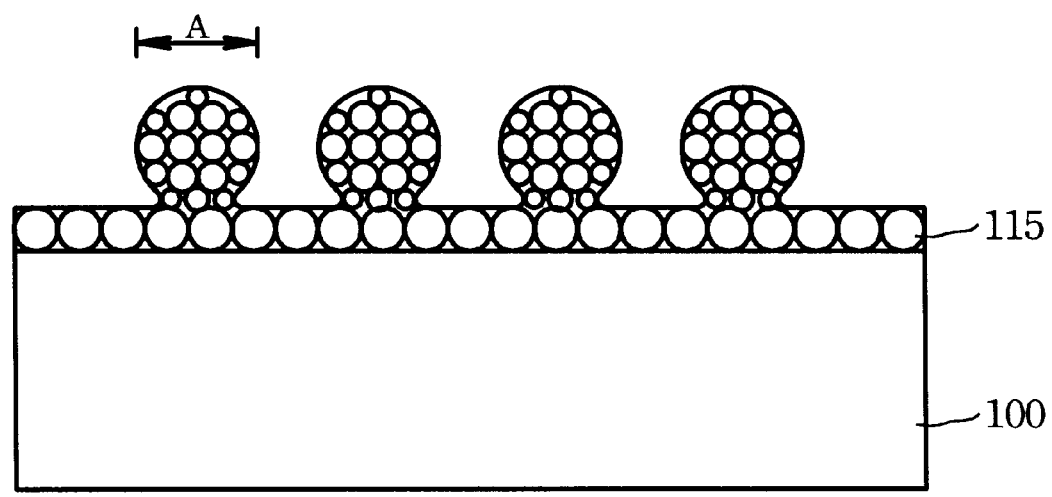
FIG. 2 shows a cross-section view of a semiconductor substrate in accordance with the prior art, wherein hemispherical polysilicon grains are formed on the surface of the substrate and the grain size of the hemispherical polysilicon grains is effected by the organic contamination on the surface of the semiconductor substrate.

Referring to FIG. 1, a semiconductor substrate 100 is provided to serve as the base of a hemispherical-grain polysilicon layer. Subsequently, an amorphous silicon layer 110 is conformally formed on the semiconductor substrate 100 by using a conventional deposition process. Referring to FIG. 2, the amorphous silicon layer 110 is transformed into a hemispherical-grain polysilicon layer 115 on the semiconductor substrate 100. Afterwards, the grain size A of the hemispherical-grain polysilicon layer 115 is measured to determine whether the semiconductor substrate 100 is suffered from organic contamination. Since the organic contamination is residual on the surface of the semiconductor substrate 100 so as that the grain size of the hemispherical-grain polysilicon layer 115 is influenced by the organic contamination and the silicon atom on the semiconductor substrate 100 can not effectively remove to form large-size hemispherical grains during the formation of the hemispherical-grain polysilicon layer 115. The grain size A noted in FIG. A has a different grain size from the grain size B noted in FIG. B, because of the organic contamination on the semiconductor substrate.

In a preferred embodiment of the present invention, the grain size of the hemispherical-grain polysilicon layer can determine whether the process environment of fabricating the layer is contaminated by organic contamination. Generally, the standard of determining the organic contamination can be used, as the concentration of the organic contamination is below 1 ppb.

While the preferred embodiment of the invention has been illustrated and described, it will be appreciated that various changes can be made therein without departing from the spirit and scope of the invention.

What is claimed is:

1. A method for detecting organic contamination in a process environment by using the deposition of hemispherical polysilicon grains, comprises:

providing a semiconductor substrate;

forming an amorphous silicon layer on the substrate;

transforming the amorphous silicon layer into a hemispherical-grain polysilicon layer on the substrate; and identifying whether the process environment of the semiconductor substrate has suffered from organic contamination by measuring the grain size of the hemispherical-grain polysilicon layer to see if the grain size is between about 0.2 to 0.4 micrometers after the transforming step.

2. The method according to claim 1, further comprises a cleaning process performed on the semiconductor substrate to remove the organic contamination on the semiconductor substrate before the hemispherical-grain polysilicon layer is formed.

3. The method according to claim 2, wherein the cleaning process cleans the semiconductor substrate by using acetone solution.

4. The method according to claim 1, wherein the organic contamination comprises the contamination of acetone solution.

5. The method according to claim 1, wherein the organic contamination has influence with the growth of the hemispherical-grain polysilicon layer, so that the grain size of the hemispherical-grain polysilicon layer is smaller than 0.4 micrometers.

6. A method for determining whether a fabrication environment has suffered from organic contamination, wherein integrated circuits are in the fabrication environment, the method comprising:

forming hemispherical polysilicon grains on the integrated circuits; and identifying whether the fabrication environment has suffered from organic contamination by measuring grain sizes of the hemispherical polysilicon grains to see if the grain sizes are between about 0.2 to 0.4 micrometers after the forming step.

7. The method according to claim 6, wherein the organic contamination comprises the contamination of acetone solution.

8. A method for detecting organic contamination in a process environment by using the deposition of hemispherical polysilicon grains, comprises:

providing a semiconductor substrate;

forming an amorphous silicon layer on the substrate;

transforming the amorphous silicon layer into a hemispherical-grain polysilicon layer on the substrate; and measuring the grain size of the hemispherical-grain polysilicon layer to identify whether the process environment of the semiconductor substrate has suffered from organic contamination.

9. The method according to claim 8, wherein the grain size of the hemispherical-grain polysilicon layer is measured, with grain size between about 0.2 to 0.4 micrometers showing that the organic contamination is residual on the semiconductor substrate; and with grain size between about 0.5 to 0.8 micrometers showing that the organic contamination is not residual on the semiconductor substrate.

10. The method according to claim 8, further comprises a cleaning process performed on the semiconductor substrate to remove organic contamination on the semiconductor substrate before the hemispherical-grain polysilicon layer is formed.

11. The method according to claim 10, wherein the cleaning process cleans the semiconductor substrate by using acetone solution.

12. The method according to claim 8, wherein the organic contamination comprises the contamination of acetone solution.

13. The method according to claim 8, wherein the organic contamination has influence with the growth of the hemispherical-grain polysilicon layer, so that the grain size of the hemispherical-grain polysilicon layer is smaller than 0.4 micrometers.

14. The method according to claim 8, wherein a determination that the process environment has suffered from the organic contamination indicates that the semiconductor substrate has suffered from the organic contamination.

\* \* \* \* \*